(12) United States Patent
Volden et al.

(10) Patent No.: US 10,188,420 B2
(45) Date of Patent: Jan. 29, 2019

(54) AORTIC PUNCH

(71) Applicant: Medline Industries, Inc., Mundelein, IL (US)

(72) Inventors: Bradley Volden, Milwaukee, WI (US); Alan Genender, Northbrook, IL (US); Derek Roberts, Chicago, IL (US); Brendan Fong, Riverwoods, IL (US)

(73) Assignee: Medline Industries, Inc., Northfield, IL (US)

( * ) Notice: Subject to any disclaimer, the term of this patent is extended or adjusted under 35 U.S.C. 154(b) by 222 days.

(21) Appl. No.: 15/294,169

(22) Filed: Oct. 14, 2016

(65) Prior Publication Data

US 2018/0103975 A1 Apr. 19, 2018

(51) Int. Cl.
*A61B 17/3205* (2006.01)
*A61B 17/00* (2006.01)

(52) U.S. Cl.
CPC .......... *A61B 17/32053* (2013.01); *A61B 2017/00778* (2013.01); *A61B 2017/00836* (2013.01); *A61B 2017/00991* (2013.01)

(58) Field of Classification Search
CPC .... A61B 17/32053; A61B 2017/00247; A61B 2017/00252; A61B 17/34; A61B 2017/1107; A61B 2017/1135; A61B 17/3205; A61B 2017/00836; A61B 2017/00991

See application file for complete search history.

(56) References Cited

U.S. PATENT DOCUMENTS

| | | |
|---|---|---|
| 1,974,418 A | 9/1934 | Cornell, Jr. |
| 4,018,228 A | 4/1977 | Goosen |
| 4,216,776 A | 8/1980 | Downie |
| D281,721 S | 12/1985 | Scanlan |
| 5,129,913 A | 7/1992 | Ruppert |
| D372,310 S | 7/1996 | Hartnett |
| 5,827,316 A | 10/1998 | Young |
| 5,910,153 A | 6/1999 | Mayenberger |
| 6,080,173 A | 6/2000 | Williamson |
| 6,080,176 A | 6/2000 | Young |
| 6,176,867 B1 | 1/2001 | Wright |
| 6,776,787 B2 | 8/2004 | Phung |
| 7,241,302 B2 | 7/2007 | Sniffen |
| 7,258,694 B1 | 8/2007 | Choi |
| 7,322,999 B2 | 1/2008 | Kanner |
| 8,956,377 B2 | 2/2015 | Khalapyan |
| 2013/0012977 A1* | 1/2013 | Khalapyan ....... A61B 17/32053 606/184 |

* cited by examiner

*Primary Examiner* — Katrina Stransky
(74) *Attorney, Agent, or Firm* — Fitch, Even, Tabin & Flannery LLP (57) ABSTRACT

Disclosed is an aortic punch comprising a first body member having a proximal end and a distal end, a second body member disposed at least partially within said first body member, a manual actuator, a piston having an anvil disposed at a distal end thereof, and a shear, said shear being integral with said second body member. The first body member and second body member are axially movable relative to one another between a fully extended position and a fully retracted position and within a range of intermediate positions while maintaining the piston and shear in position relative to each other in the axial direction, and separately the shear is axially movable via manual actuation relative to said anvil between an insertion position and a shearing position and a range of intermediate positions.

19 Claims, 11 Drawing Sheets

AORTIC PUNCH

TECHNICAL FIELD

This invention relates generally to hand held medical devices, and more specifically relates to hand held medical devices having extendable bodies.

BACKGROUND

In some medical procedures, such as a coronary artery bypass graft surgery, it is necessary to create a uniform round hole in the aorta or other blood channel. It is known in the art to employ an aortic punch to create such holes. In operation, a small incision is created in the aorta through which the anvil of the aortic punch is passed. The wall of the aorta is then pinched between the anvil and the shear of the aortic punch in order to create the hole.

Currently aortic punches are available in a variety of sizes to accommodate doctors with varying hand sizes and preferences. As a result, suppliers and hospitals generally may have to stock a variety of sizes of aortic punches. It would be useful to provide an aortic punch that has an adjustable length so that a single device can meet varying surgeon preferences.

DETAILED DESCRIPTION

The aortic punch shown in the Figures is configured to telescope such that the user may adjust the overall length of the device without actuating the device, and independently may adjust the distance between the anvil and the shear to actuate the device.

FIGS. 1-5 illustrate an aortic punch 100 comprising an outer body member or first body member 110, a second body member 120, a shear 130, a piston 140, and a manual actuator assembly 150 terminated at an interface 154. As show, the second body member 120 is in a fully retracted state, and the anvil 142 is in an insertion position relative to the shear 130. In this position the piston 140 is extended relative to the shear 130 such that the anvil 142 is exposed and spaced apart from the shear 130. This is the anvil position intended for tissue insertion in normal use, wherein the anvil 142 is placed inside the aorta (not shown) via a small incision and the shear 130 and piston 140 are then moved relative to each other such that the anvil 142 passes into the shear 130 thereby placing the anvil into a shearing position. As the anvil 142 enters the shear 130, the wall of the aorta is pinched therebetween to create a clean-edged round hole in the aortic tissue.

Figure 1:
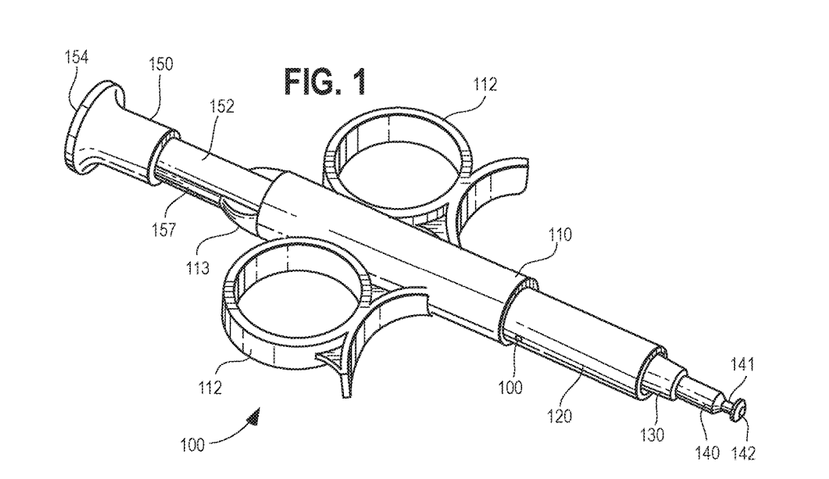
FIG. 1 is a perspective view of an aortic punch in accordance with one embodiment, depicting the anvil of the punch in an insertion position and the second body of the punch in a fully retracted position.
Figure 2:
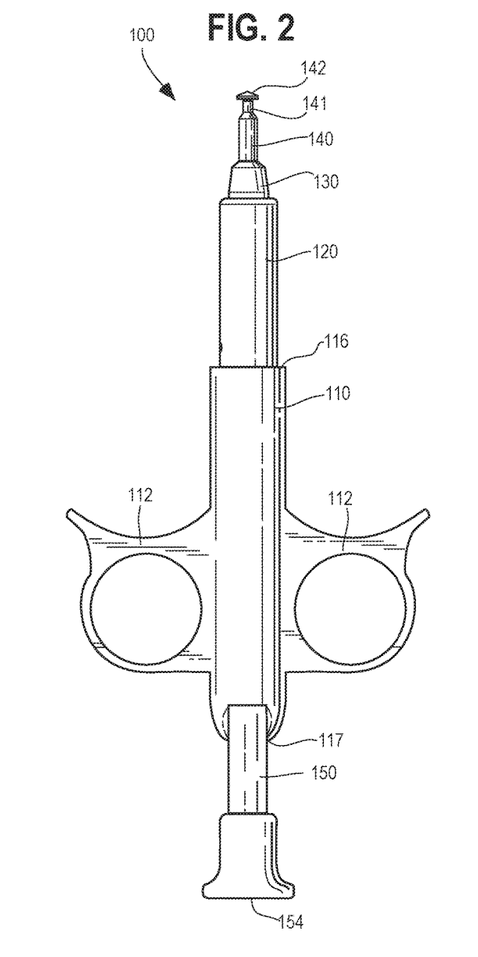
FIG. 2 is a front elevational view of the aortic punch depicted in FIG. 1, again depicting the anvil in an insertion position and the second body in a fully retracted position.
Figure 6:
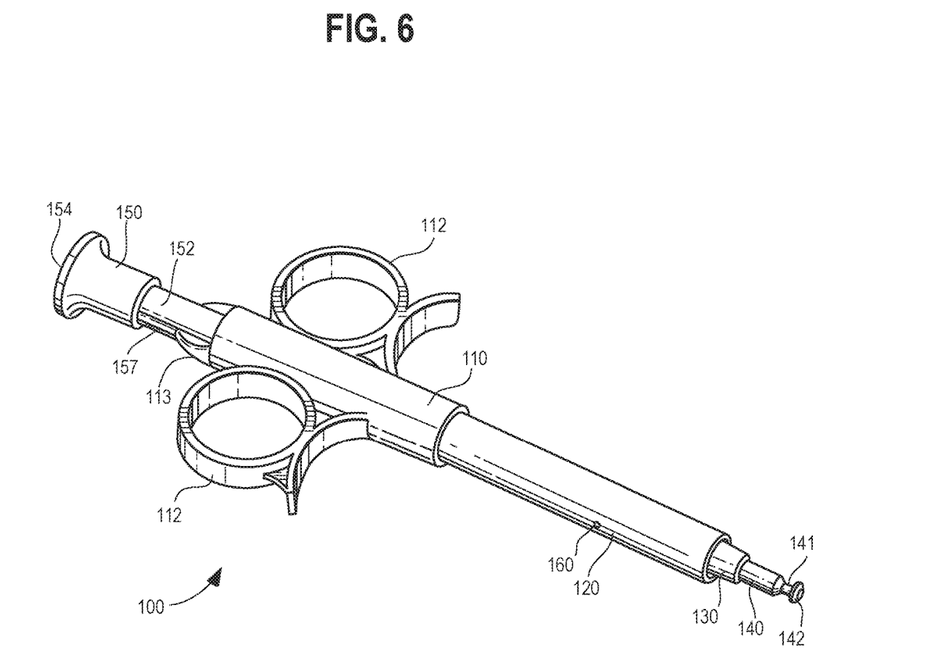
FIG. 6 is a perspective view of the aortic punch depicted above, depicting the anvil in an insertion position and the second body in a fully extended position.
Figure 7:
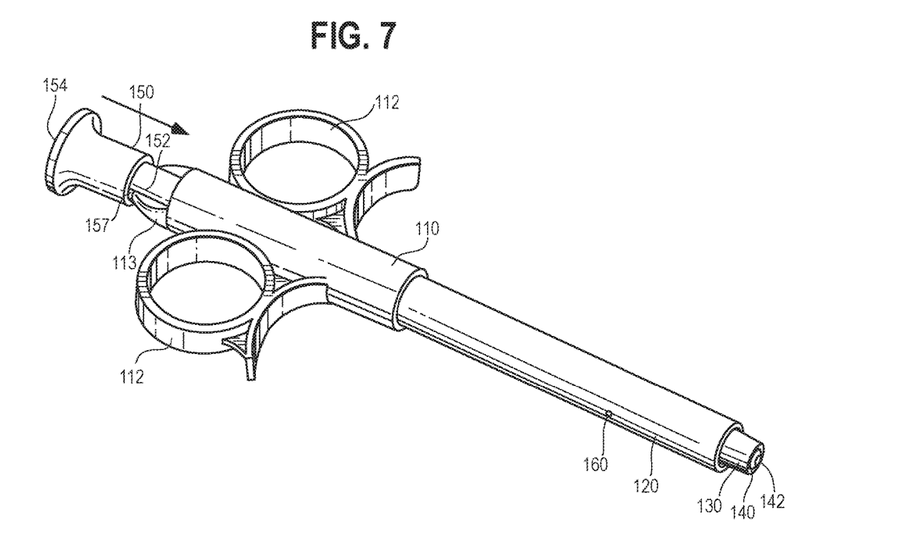
FIG. 7 is a perspective view of the aortic punch depicted above, depicting the anvil in a shearing position and the second body in a fully extended position.

The first body member 110 is sized to be gripped by a user and includes finger holes 112 disposed on an outer surface thereof. The second body member 120 is sized to be at least partially received within the first body member 110 at a distal end 116 of the first body member 110. The manual actuator assembly 150 further includes a user interface configured to be manually actuated by the user, the interface being a thumb press 154 in the illustrated embodiments. As discussed in more detail below, the aortic punch 100 can undergo two types of actuation of movement. First, the second body member 120 is configured to travel between a fully retracted position and a fully extended position and a range of intermediate positions relative to the first body member. When the second body member 120 is moved from a fully retracted position, as shown in FIG. 1, to a fully extended position, as shown in FIG. 6, the distance between the anvil 142 and the shear 130 remains constant or substantially so, and likewise the distance between the thumb press 154 and the first body member 110 remains constant or substantially so. The second type of movement is of the anvil 142 relative to the shear 130, where these parts are movable between an insertion position (FIG. 1) and a shearing position (FIG. 7). As discussed in more detail hereinbelow, the thumb press 154 may be depressed to thereby move the anvil 142 and shear 130 relative to each other from the insertion position to the shearing position.

Figure 3:
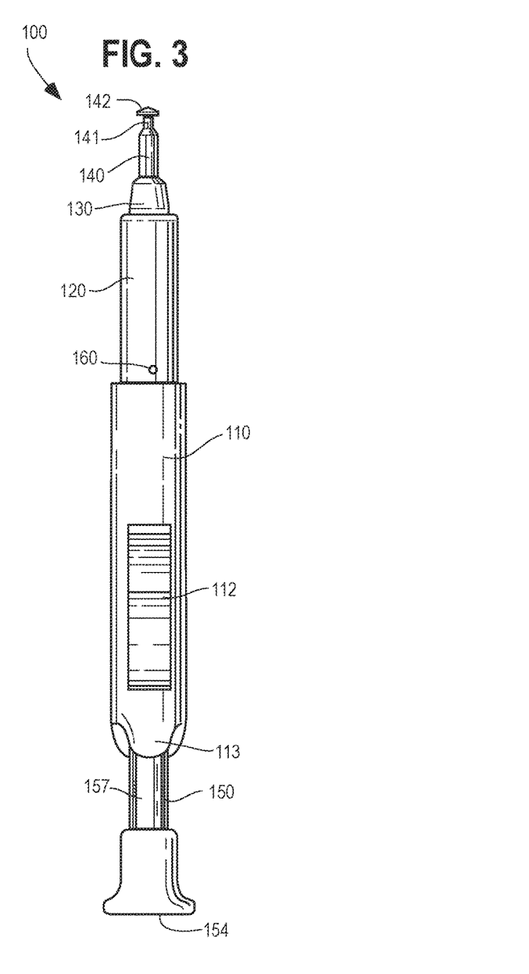
FIG. 3 is a side elevational view of the aortic punch depicted in FIGS. 1 and 2.
Figure 4:
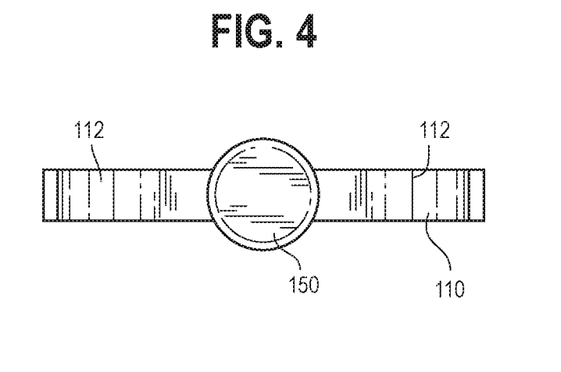
FIG. 4 is a top plan view of the aortic punch depicted in FIGS. 1-3.
Figure 5:
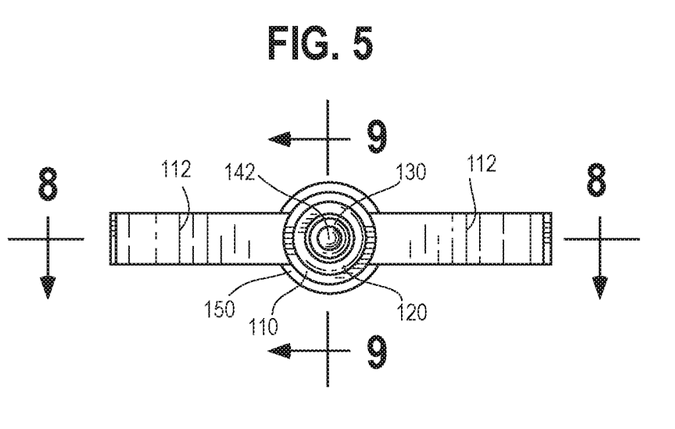
FIG. 5 is a bottom plan view of the aortic punch depicted in FIGS. 1-4.
Figure 16:
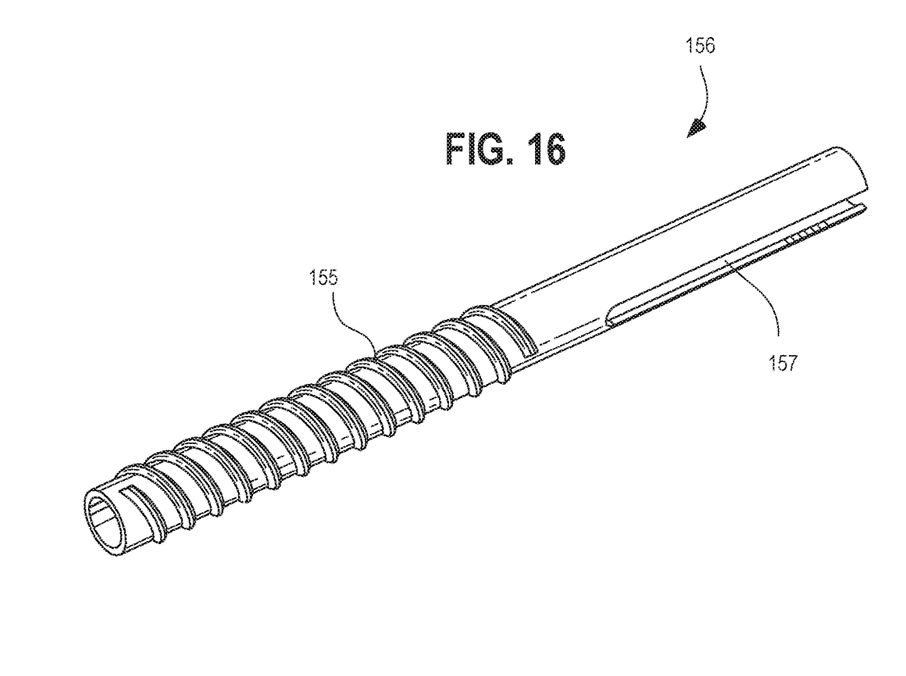
FIG. 16 is a perspective view of the actuator member of the aortic punch shown above.

The manual actuator assembly 150 includes an actuator member 156 having a proximal end 152 that extends from the first body member 110 at a proximal end 117 of the first body member 110. The actuator member 156 is integrally connected to the thumb press 154 at the actuator member proximal end 152. As best seen in FIGS. 1, 3, and 16, the actuator member 156 has at least one groove or slot 157 into which projections 113 of the first body member are at least partially received to thereby inhibit the actuator member 156 from rotating relative to the first body member 110. In the embodiment shown in FIGS. 1-16 the manual actuator assembly 150 is configured as a plunger. In alternative embodiments, the manual actuator can have different configuration such as a trigger or a twist operated design.

The anvil 142 is disposed at the distal end of the piston 140 and is separated from the remainder of the piston 140 by an annular recess 141 in the piston 140. The maximum outer diameter 143 (FIG. 3) of the anvil 142 is just slightly smaller than the inner diameter of the shear 130, such that the anvil 142 can fit precisely into the shear 130 to enable the shear and anvil to cooperate to make a clean tissue cut.

With reference now to FIGS. 8-13, the first body member 110 includes a first inner member 114 that contains a thread 115 (also shown in FIG. 8) on the internal surface. The thread of the first inner member 114 engages externally facing thread 121 (also shown in FIG. 8) on the piston 140. The threads 115 and 121 each have a first pitch 105 (referenced in FIG. 8). It is contemplated that a multiple-threaded configuration alternatively may be provided.

The actuator member 156 has an externally facing thread 155. The thread 155 engages an internal thread 159 of the second body member 120. The pitch of the thread 155 on the actuator member 156 and the thread 159 of the second body member 120 is identical to the first pitch 105. Again, it is contemplated that a multiple-threaded configuration may be provided.

Figure 9:
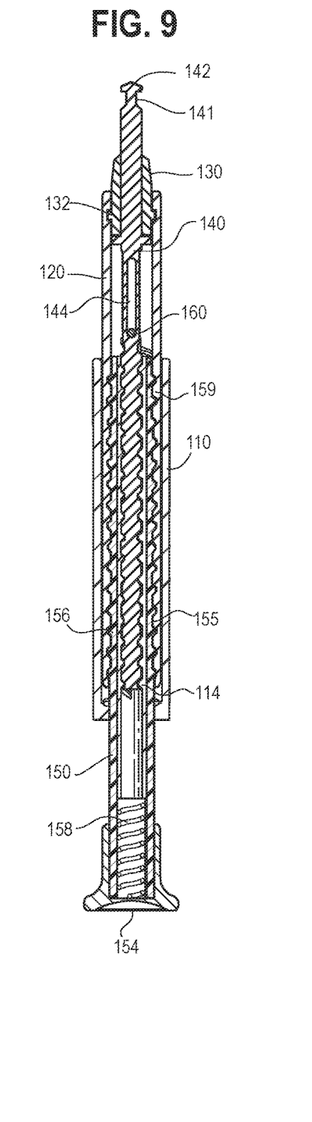
FIG. 9 is a side cross-sectional taken along line 9-9 in FIG. 5, again depicting the anvil in an insertion position and the second body in a fully retracted position.
Figure 10:
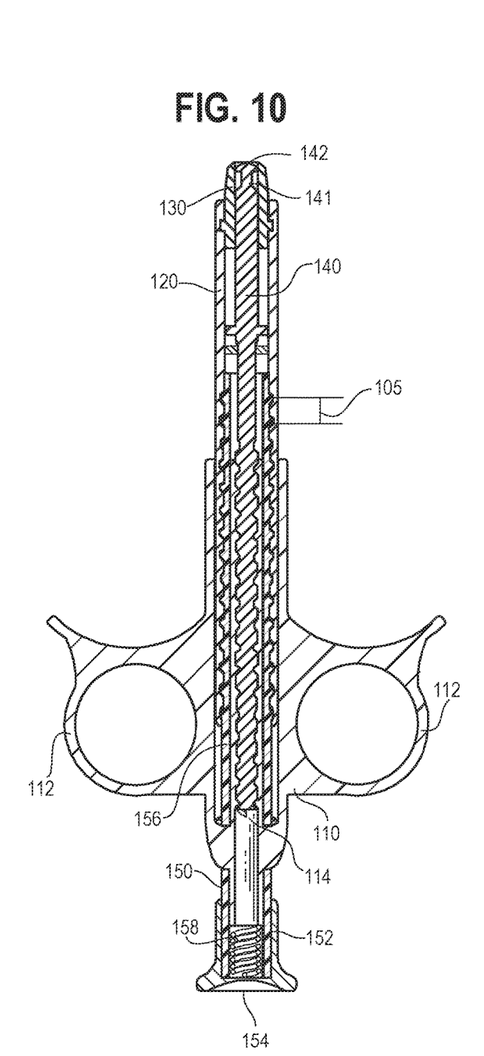
FIG. 10 is a cross-sectional view of the aortic punch shown in FIG. 8, except that the anvil is now depicted in a shearing position and the second body in a fully retracted position.

With reference to FIG. 9, the shear 130 includes an annular flange 132 that is seated within a corresponding recess or groove in the second body member 120. This prevents the shear 130 from axially translating relative to the second body member 120. In alternative embodiments, the shear may be integral with the second body member or may be connected to the second body member 120 in another way that prevents relative axial translation such as a threaded connection or an arrangement where the shear is held in place by a set screw or pin. The aortic punch 100 further includes a spring 158 that is positioned between the thumb press 154 and the proximal end 117 of the first body member 110.

Figure 11:
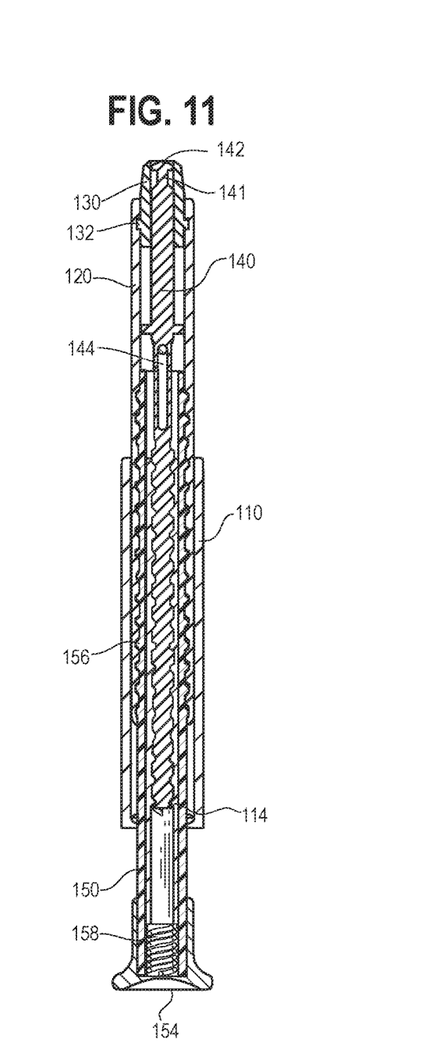
FIG. 11 is a cross-sectional view of the aortic punch shown in FIG. 9, except that the anvil is now depicted in a shearing position and the second body in a fully retracted position.
Figure 12:
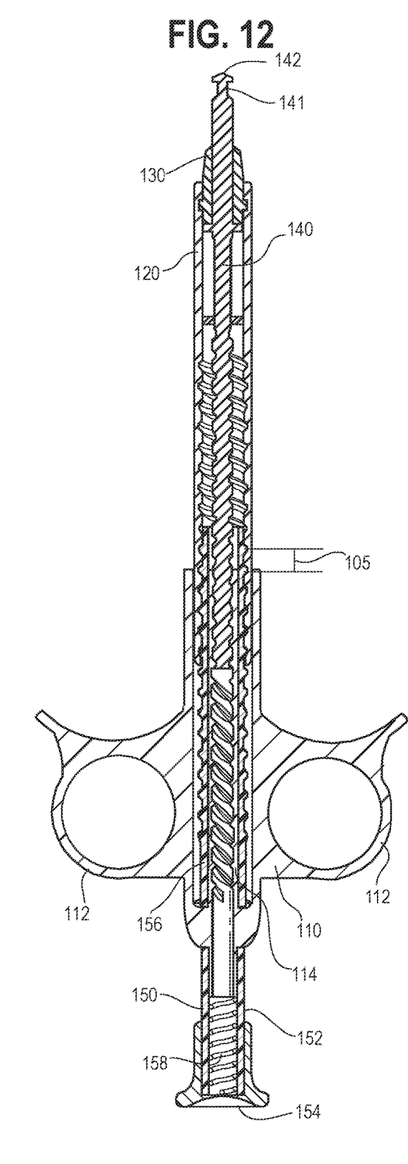
FIG. 12 is a cross-sectional view of the aortic punch shown in FIG. 10, depicting the anvil in an insertion position and the second body in a fully extended position.

To actuate the punch, the user inserts his or her fingers into the finger holes 112 and depresses the thumb press. The actuator member 156 and the second body member 120 remain in threaded engagement and cannot slide to translate relative to one another, and likewise the piston 140 and first inner member 114 remain in threaded engagement and cannot slide to translate relative to one another. Accordingly, the user's depression of the thumb press 154 causes the second body member 120 and the actuator member 126 to move as a unit. This causes axial translation of the second body member 120 relative to the first body member 110, thereby causing the shear 130 to advance relative to the piston 140 and anvil 142. As shown in FIGS. 9 and 11, the pin 160 slides in the slot 144 of the piston 140 when the aortic punch 100 is actuated. The shear advances to just cover the largest diameter of the anvil 142 to thereby shear away a neat circular hole in the aortic tissue.

When the thumb press 154 is depressed with the anvil held stationary inside a tissue incision, the actuator member 156 is urged away from the user, thereby causing the shear 130 to move towards the anvil 142. This also causes the spring 158 to become compressed. When the user releases pressure on the thumb press 154, the spring 158 decompresses, biasing the thumb press 154 and actuator member 156 towards the user and causing the shear 130 to return to its initial position relative to the anvil 142 thereby returning the anvil to the insertion position relative to the shear. In alternative embodiments, it is contemplated that the spring 158 may be positioned elsewhere within the punch 100 and otherwise configured to return the shear to its original position.

Figure 8:
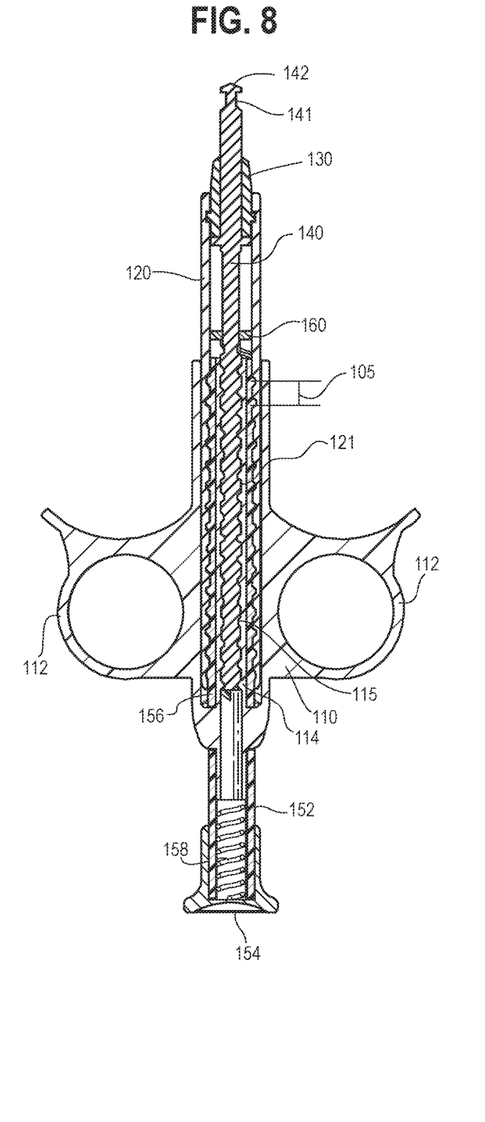
FIG. 8 is a front cross-sectional view taken along line 8-8 in FIG. 5, of the aortic punch shown above, depicting the anvil in an insertion position and the second body in a fully retracted position.
Figure 14:
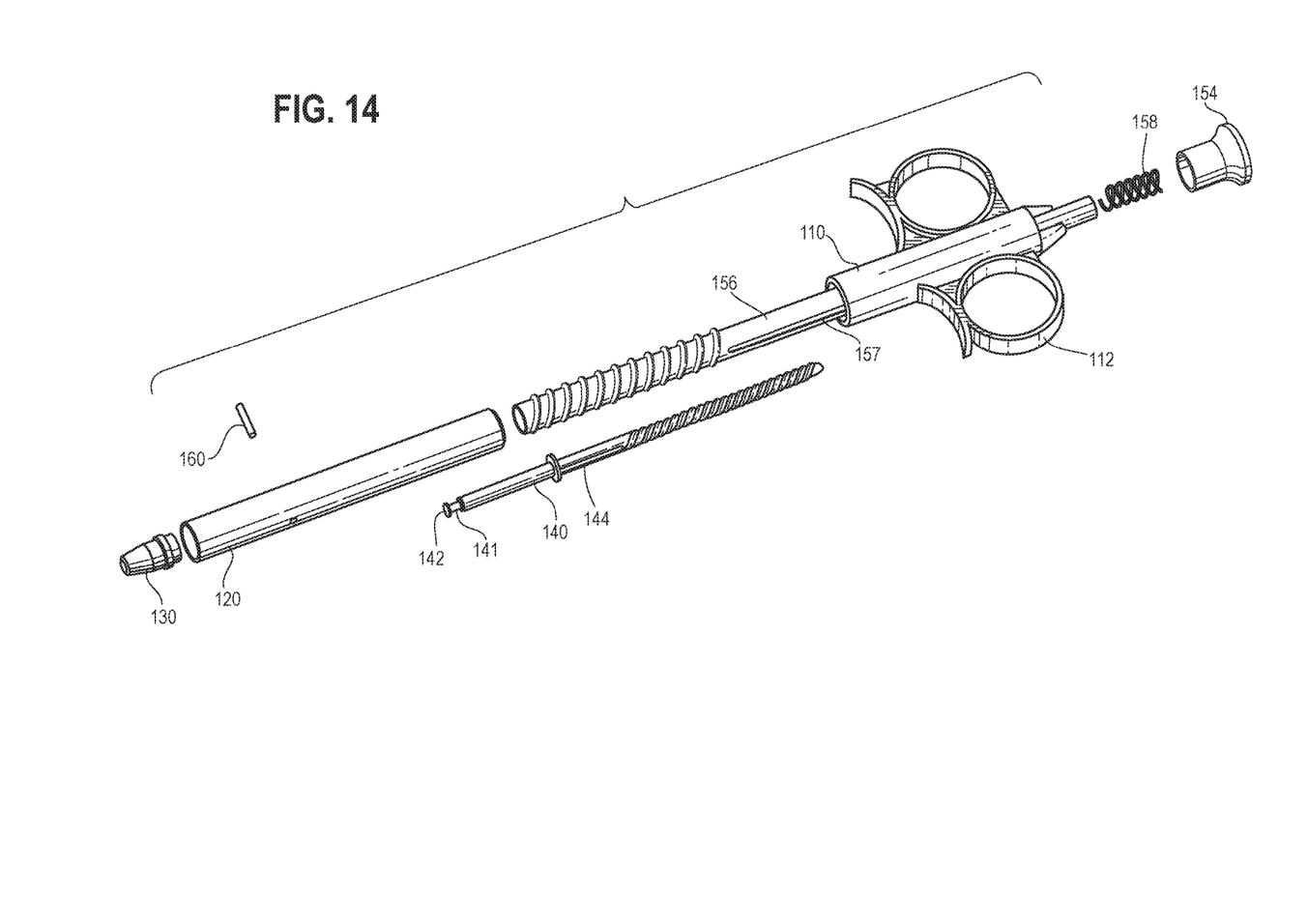
FIG. 14 is an exploded view of the aortic punch shown above.

As seen for example in FIGS. 8, 9, and 14, a pin 160 extends through the second body member 120 and the piston 140. The pin 160 prevents the piston 140 from rotating relative to the second body member 120. As best shown FIG. 9, the piston 140 includes a slot 144 through which the pin 160 passes. This arrangement allows the piston 140 to move axially relative to the pin 160 which is rigidly attached to the second body member 120, but prevents the piston 140 from rotating about its axis relative to the pin 160.

The user may wish to adjust the length of the punch 100 prior to use. To transition the second body member 120 from a fully retracted position (see FIG. 8) to a fully extended position (see FIG. 12) or to positions therebetween, the user rotates the second body member 120 relative to the first body member 110. Because the pin 160 engages the slot 144, as the second body member 120 rotates, the piston 140 is urged to rotate simultaneously to the same degree as the second body member. Similarly, as the first body member 110 rotates, the cooperation of the projection 113 and the groove 157 urge the actuator member 156 to rotate.

As the first and second body members rotate relative to one another, the thread 159 of the second body member cooperates with the thread 155 of the actuator member 150 to thereby advance the second body member relative to the actuator in the manner of a screw. At the same time, the thread 121 of the piston 140 cooperates with the thread 115 of the first inner member 114 of the first body member 120 to thereby advance the piston 140 towards the distal direction, again in the manner of a screw. Because all of the threads have the same pitch 105 and are rotating by the same amount, the piston 140 moves axially relative to the actuator 150 and hence relative to the first body member 110 to the same extent that the second body member 120 moves axially relative to the manual actuator 150. The position of the first body member 110 relative to the thumb press 154 remains constant (or very nearly so), and likewise the relative position of the shear 130 and the anvil 142 remains constant (or very nearly so).

Figure 13:
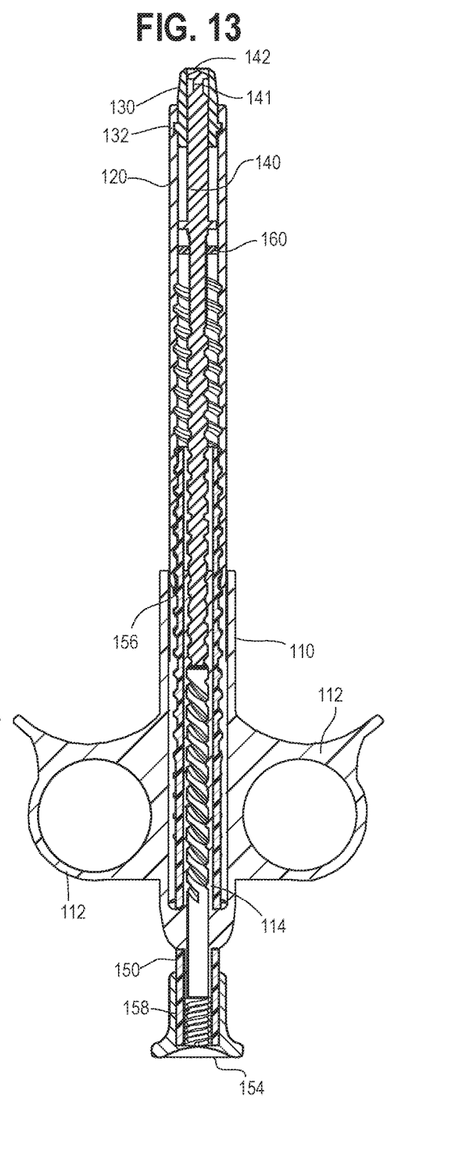
FIG. 13 is a cross-sectional view of the aortic punch shown in FIG. 12 with the anvil in a shearing position.

When the second body member is fully extended, as shown in FIG. 13, there is no change in the manner of actuation of punch 100. The user uses the thumb press to cause the manual actuator 150 to move the anvil 142 relative to the shear 130 to again create a neat and clean hole in the aortic tissue.

Figure 15:
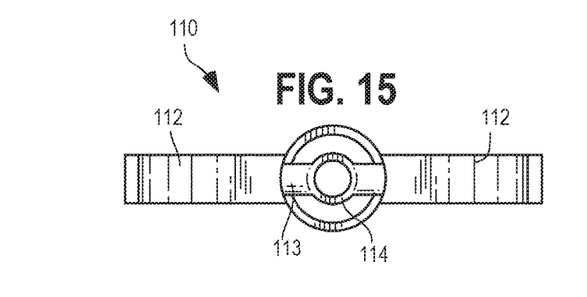
FIG. 15 is a top plan view of the first body member of the aortic punch shown above.

As shown in FIG. 14, the actuator member 156 is hollow. An internal portion of the projection 113 of the first body member 110 is disposed within the groove 157 and supports the first internal member 114 (as best shown in FIG. 15). The internal portion slides within the groove 157 when the manual actuator 150 is actuated. The cooperation of the internal portion and the groove 157 further prevents rotation of the actuator member 156 relative to the first body member 110.

Figures 17, 18:
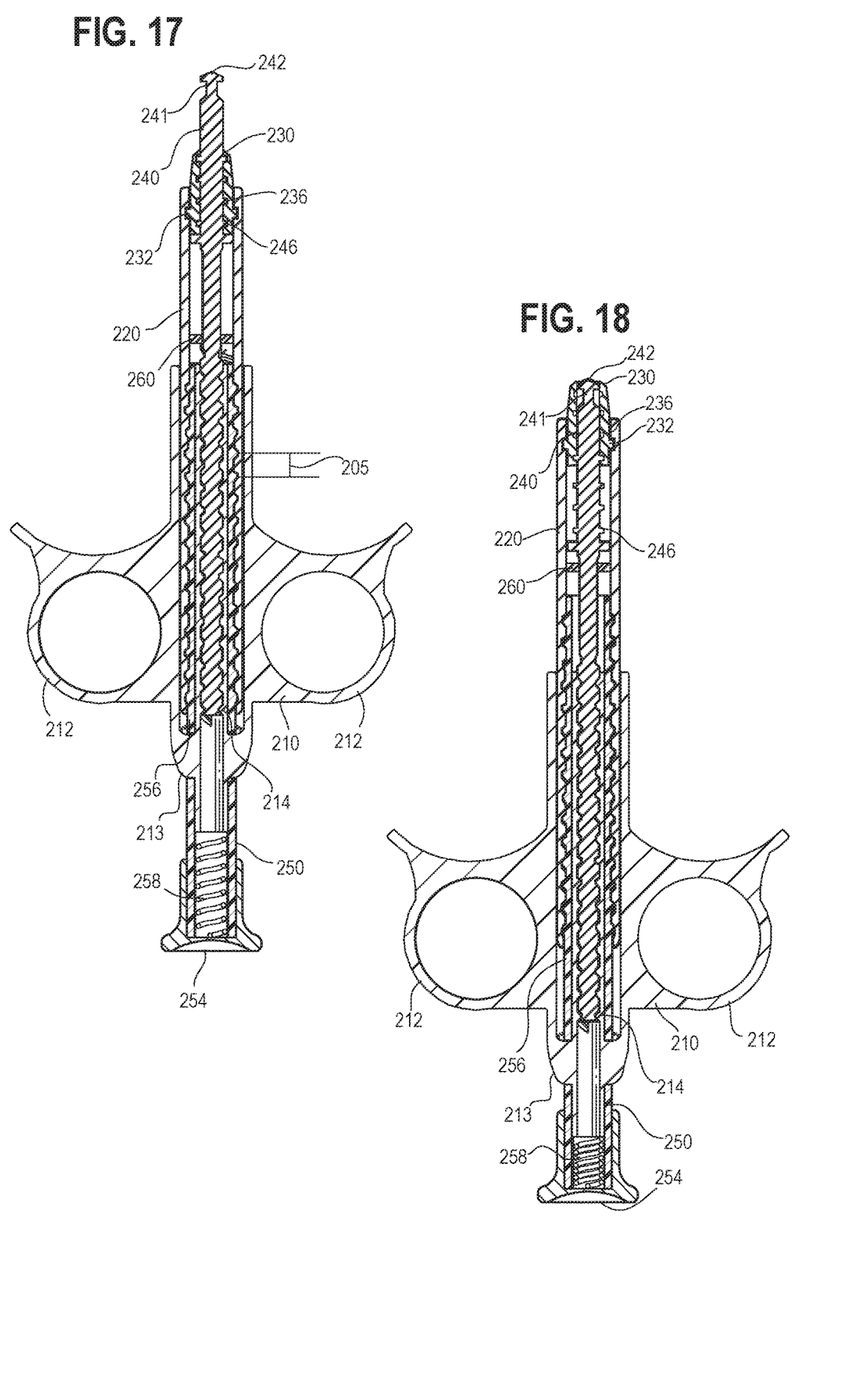
FIG. 17 is a cross-sectional view of an alternative embodiment of the aortic punch, depicting the anvil in an insertion position.
FIG. 18 is a cross-sectional view of the punch depicted in FIG. 13, depicting the anvil in a shearing position.

With reference now to the alternative aortic punch 200 shown in FIGS. 17 and 18, the illustrated aortic punch 200 differs from the aortic punch 100 in the addition of internal thread 236 of the shear 230. A second external thread 246 of the piston engages the internal threads 236 of the shear 230. The threads 236, 246 have a pitch that is greater than the pitch 205 of the other threads of the punch 200. When the manual actuator 250 is actuated, the threads 236, 246 cooperate in the manner of a screw to induce rotation of the shear 230 relative to the piston 240, whereby flange 232 has some freedom of movement within the second body member 220. This results in some relative rotation of the shear 230 relative to the anvil 242 as the anvil and shear are moved relative to one another, thereby aiding in the shearing of the wall of the aorta.

The various component parts of the aortic punch 100 can be formed of a variety of rigid materials, so long as those materials are suitable for use in medical devices. For example, the first body member 110, second body member 120, and manual actuator 150 may be formed of a rigid plastic such as ABS or polypropylene. The shear 130 and the piston 140 may be formed of a corrosion resistant metal such as stainless steel or zinc plated steel. The device may be made to any suitable dimensions. For example, the threaded portions may be approximately 2.5 in. long, enabling aortic punch 100 to be adjusted from approximately 5.5 in. total length to approximately 8 in. total length.

In alternative embodiments, the same telescoping mechanism described herein may be implemented in medical devices, or even nonmedical devices, other than an aortic punch. Such devices may include, but are not limited to, laparoscopic devices and pulse lavage devices.

It is thus seen that an aortic punch with a telescoping body may be provided and used in accordance with the foregoing teachings.

Uses of singular terms such as "a," "an," are intended to cover both the singular and the plural, unless otherwise indicated herein or clearly contradicted by context. The terms "comprising," "having," "including," and "containing" are to be construed as open-ended terms. Any description of certain embodiments as "preferred" embodiments, and other recitation of embodiments, features, or ranges as being preferred, or suggestion that such are preferred, is not deemed to be limiting. The invention is deemed to encompass embodiments that are presently deemed to be less preferred and that may be described herein as such. All methods described herein can be performed in any suitable order unless otherwise indicated herein or otherwise clearly contradicted by context. The use of any and all examples, or exemplary language (e.g., "such as") provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context. The description herein of any reference or patent, even if identified as "prior," is not intended to constitute a concession that such reference or patent is available as prior art against the present invention. No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service.

What is claimed is:

1. An aortic punch comprising:
   a first body member having a proximal end and a distal end;
   a second body member disposed at least partially within said first body member;
   a manual actuator;
   a piston having an anvil disposed at a distal end thereof; and
   a shear, said shear being integral with said second body member;
   wherein the first body member and second body member are axially movable relative to one another between a fully extended position and a fully retracted position and within a range of intermediate positions while maintaining the piston and shear in position relative to each other in the axial direction,
   wherein separately the shear is axially movable via manual actuation relative to said anvil between an insertion position and a shearing position and a range of intermediate positions, and
   wherein said piston includes external threads and wherein said first body member includes an internal surface with internal threads, the external threads of the piston engaging the internal threads of the internal surface of the first body member.

2. The aortic punch of claim 1, said manual actuator comprising a plunger, said plunger comprising an actuator member having external threads, the second body member including an internal surface with internal threads, the threads of the actuator member of the plunger engaging the threads of the internal surface of the second body member.

3. The aortic punch of claim 1,
   wherein said piston includes external threads having a first pitch and wherein said first body member includes a first inner member having an internal surface with internal threads, the external threads of the piston engaging the internal threads of the internal surface of the first inner member,
   wherein said manual actuator comprises a plunger, said plunger comprising an actuator member having external threads having a second pitch equal to the first pitch, the second body member including an internal surface with internal threads, the threads of the actuator member of the plunger engaging the threads of the internal surface of the second body member,
   wherein said actuator member has a surface that engages a mating surface on said first body member so as to prevent rotation of the first body member relative to the actuator member,
   wherein the first inner member has unthreaded radially outwardly disposed surface and the actuator member has unthreaded radially inwardly disposed surface, the unthreaded radially outwardly disposed surface and the unthreaded radially inwardly disposed surface being in sliding engagement to allow relative axial translation of the first and second body members,
   whereby rotation of the first and second body members relative to one another causes axial translation of the first and second body members relative to one another and also causes corresponding axial translation of the piston relative to the first body member to thereby maintain the piston and shear in position relative to each other in the axial direction.

4. The aortic punch of claim 3, further comprising a pin coupled to the second body member and the piston, the pin configured to restrict rotation of the piston with respect to the second body member.

5. The aortic punch of claim 3, said actuator member being separately formed from said manual actuator and axially rigidly affixed thereto.

6. The aortic punch of claim 1, wherein the shear comprises a threaded internal surface and the piston comprises a threaded external surface and wherein the threaded internal surface of the shear engage the threaded external surface of the piston, whereby when the shear moves axially between the insertion position and the shearing position the shear rotates relative to the anvil.

7. The aortic punch of claim 1, said manual actuator and said shear remaining in position relative to each other in the axial direction when the shear is moved axially relative to said anvil.

8. An aortic punch comprising:
   a first body member having a proximal end and a distal end;
   a second body member disposed at least partially within said first body member;
   a manual actuator;
   a piston having an anvil disposed at a distal end thereof; and
   a shear, said shear affixed to said second body member;
   wherein the first body member and second body member are axially movable relative to one another between a fully extended position and a fully retracted position and within a range of intermediate positions while maintaining the piston and shear in position relative to each other in the axial direction,
   wherein separately the shear is axially movable via manual actuation relative to said anvil between an insertion position and a shearing position and a range of intermediate positions, and
   wherein said piston includes external threads and wherein said first body member includes an internal surface with internal threads, the external threads of the piston engaging the internal threads of the internal surface of the first body member.

9. The aortic punch of claim 8, said manual actuator comprising a plunger, said plunger comprising an actuator member having external threads, the second body member including an internal surface with internal threads, the threads of the actuator member of the plunger engaging the threads of the internal surface of the second body member.

10. The aortic punch of claim 8,
    wherein said piston includes external threads having a first pitch and wherein said first body member includes a first inner member having an internal surface with internal threads, the external threads of the piston engaging the internal threads of the internal surface of the first inner member,
    wherein said manual actuator comprises a plunger, said plunger comprising an actuator member having external threads having a second pitch equal to the first pitch, the second body member including an internal surface with internal threads, the threads of the actuator member of the plunger engaging the threads of the internal surface of the second body member,
    wherein said actuator member has a surface that engages a mating surface on said first body member so as to prevent rotation of the first body member relative to the actuator member,
    wherein the first inner member has unthreaded radially outwardly disposed surface and the actuator member has unthreaded radially inwardly disposed surface, the unthreaded radially outwardly disposed surface and the unthreaded radially inwardly disposed surface being in sliding engagement to allow relative axial translation of the first and second body members,
    whereby rotation of the first and second body members relative to one another causes axial translation of the first and second body members relative to one another and also causes corresponding axial translation of the piston relative to the first body member to thereby maintain the piston and shear in position relative to each other in the axial direction.

11. The aortic punch of claim 10, further comprising a pin coupled to the second body member and the piston, the pin configured to restrict rotation of the piston with respect to the second body member.

12. The aortic punch of claim 10, said actuator member being separately formed from said manual actuator and axially rigidly affixed thereto.

13. The aortic punch of claim 8, wherein the shear comprises a threaded internal surface and the piston comprises a threaded external surface and wherein the threaded internal surface of the shear engage the threaded external surface of the piston, whereby when the shear moves axially between the insertion position and the shearing position the shear rotates relative to the anvil.

14. The aortic punch of claim 8, said manual actuator and said shear remaining in position relative to each other in the axial direction when the shear is moved axially relative to said anvil.

15. The aortic punch of claim 8, wherein the first body member is rotationally coupled to the manual actuator so as to restrict rotation of the manual actuator relative to the first body member, and wherein the second body member is coupled to the piston so as to restrict rotation of the piston relative to the second body member.

16. An aortic punch comprising:
    a first body member having a proximal end and a distal end;
    a second body member disposed at least partially within said first body member;
    a manual actuator;
    a piston having an anvil disposed at a distal end thereof; and
    a shear, said shear affixed to said second body member;
    wherein the first body member and second body member are axially movable relative to one another between a fully extended position and a fully retracted position and within a range of intermediate positions such that the axial distance between the shear and the first body member increases as the second body is moved from the fully retracted position to the fully extended position while maintaining the piston and shear in position relative to each other in the axial direction, and
    wherein separately the shear is axially movable via manual actuation relative to said anvil between an insertion position and a shearing position and a range of intermediate positions.

17. The aortic punch of claim 16, wherein said piston includes external threads and wherein said first body member includes an internal surface with internal threads, the external threads of the piston engaging the internal threads of the internal surface of the first body member.

18. The aortic punch of claim 16, said manual actuator and said shear remaining in position relative to each other in the axial direction when the shear is moved axially relative to said anvil.

19. The aortic punch of claim 16, wherein the first body member is rotationally coupled to the manual actuator so as to restrict rotation of the manual actuator relative to the first body member, and wherein the second body member is coupled to the piston so as to restrict rotation of the piston relative to the second body member.

\* \* \* \* \*